United States Patent [19]

Tankovich et al.

[11] Patent Number: 5,752,949

[45] Date of Patent: *May 19, 1998

[54] HAIR REMOVAL METHOD

[75] Inventors: Nikolai I. Tankovich; Zhong-Quan Zhao; Paul Fairchild, all of San Diego, Calif.

[73] Assignee: ThermoLase Corporation, San Diego, Calif.

[*] Notice: The term of this patent shall not extend beyond the expiration date of Pat. No. 5,425,728.

[21] Appl. No.: 644,231

[22] Filed: May 13, 1996

Related U.S. Application Data

[63] Continuation-in-part of Ser. No. 489,358, Jun. 12, 1995, Ser. No. 492,283, Jun. 19, 1995, and Ser. No. 280,928, Jul. 26, 1994, abandoned, each is a continuation-in-part of Ser. No. 5,810, Jan. 19, 1993, Pat. No. 5,425,728, which is a continuation-in-part of Ser. No. 783,789, Oct. 2, 1991, Pat. No. 5,226,907.

[51] Int. Cl.$^6$ .............................. A61B 17/36; A61B 17/50
[52] U.S. Cl. .................................................. 606/9; 606/133
[58] Field of Search ........................... 606/1, 9, 131, 606/133; 128/898

[56] References Cited

U.S. PATENT DOCUMENTS

| | | |
|---|---|---|
| 3,538,919 | 11/1970 | Mayer. |
| 3,693,623 | 9/1972 | Harte et al. |
| 3,769,963 | 11/1973 | Goldman et al. |
| 3,794,028 | 2/1974 | Mueller et al. |
| 3,834,391 | 9/1974 | Block. |
| 3,900,034 | 8/1975 | Katz et al. |
| 4,336,809 | 6/1982 | Clark. |
| 4,388,924 | 6/1983 | Weissman et al. |
| 4,461,294 | 7/1984 | Baron. |
| 4,608,978 | 9/1986 | Rohr. |
| 4,617,926 | 10/1986 | Sutton. |
| 4,712,543 | 12/1987 | Baron. |
| 4,813,412 | 3/1989 | Yamazaki. |
| 5,059,192 | 10/1991 | Zaias. |
| 5,423,803 | 6/1995 | Tankovich et al. ............... 606/131 |
| 5,425,728 | 6/1995 | Tankovich ........................ 606/131 |

FOREIGN PATENT DOCUMENTS

| | | |
|---|---|---|
| 1041610 | 6/1974 | Canada. |
| 1208702 | 7/1986 | Canada. |
| EPD64967A2 | 4/1995 | European Pat. Off. |
| 2267122 | 4/1975 | France. |
| 2595239 | 6/1982 | France. |

(List continued on next page.)

OTHER PUBLICATIONS

Porphyrins in Tumor Phototherapy—Andereoni 1984—pp. 143–155.

Investigation and Therapy in Dermatology A. Anders, et al.—Conf. Laser 77 Optics–Electronics (20–24 Jun. 1977).

*Primary Examiner*—Glenn K. Dawson
*Attorney, Agent, or Firm*—Fish & Richardson P.C.

[57] ABSTRACT

A process for the long term or permanent prevention of growth of unwanted hair. The upper portions of hair ducts (i.e. portions near the skin surface) in a section of skin are infiltrated with a contaminant having a high absorption at at least one frequency band of light. The skin is then illuminated using a process having at least two distinct phases. In a "mechanical" phase the skin section is illuminated (e.g., by a laser) with at least one short pulse of light sufficient to cause tiny explosions in the contaminant forcing portions of the contaminant more deeply into the hair ducts. During a "thermal" phase the skin section is then illuminated so as to heat the contaminant substantially without further explosion or vaporization of the contaminant. The hot contaminant heats portions of the skin tissue immediately surrounding the contaminant to a temperature high enough and for a long enough period of time to devitalize the tissue. The process may also include a "cleanup" phase, during which the skin section is illuminated with a few short pulses of light to cause additional explosions in and vaporization of portions of the contaminant then remaining in the ducts and additional damage to the skin tissue immediately surrounding the contaminant.

28 Claims, 7 Drawing Sheets

FOREIGN PATENT DOCUMENTS

| | | |
|---|---|---|
| 2590791 | 6/1987 | France . |
| 2515697 | of 0000 | Germany . |
| 3220902 | 6/1982 | Germany . |
| 63-249577 | 10/1988 | Japan . |
| 8002640 | 12/1980 | WIPO . |
| 8602783 | 5/1986 | WIPO . |
| WO90/11797 | 10/1990 | WIPO . |
| 9104073 | 4/1991 | WIPO . |
| WO91/13652 | 9/1991 | WIPO . |
| WO91/13653 | 9/1991 | WIPO . |
| WO93/21842 | 11/1993 | WIPO . |
| WO93/21992 | 11/1993 | WIPO . |

HAIR REMOVAL METHOD

CROSS REFERENCES TO RELATED APPLICATIONS

This application is a continuation in part of Ser. No. 08/489,358 filed Jun. 12, 1995, Ser. No. 08/492,283 filed Jun. 19, 1995 and Ser. No. 08/280,928 filed Jun. 26, 1994 now abandoned, all of which are continuations in part of Ser. No. 005,810 filed Jan. 1, 1995 now U.S. Pat. No. 5,425,728, issued Jun. 20, 1995 which was a CIP of Ser. No. 07/783,789 filed Oct. 29, 1991 now U.S. Pat. No. 5,226,907 issued Jul. 13, 1993. The entire disclosures of U.S. Pat. Nos. 5,425,728 and 5,226,907 are incorporated herein by reference to them.

FIELD OF THE INVENTION

This invention relates to devices and methods for hair removal and in particular to the use of laser devices for hair removal and long-term prevention of hair growth.

BACKGROUND OF THE INVENTION

The principal methods presently used to attempt permanent hair removal involve the use of electrolysis techniques. These techniques involve some pain, are time consuming, and demand a fair degree of expertise in their application and normally do not guarantee a permanent effect.

The prior art of hair removal also includes attempts at removing hair with laser beams. Three such techniques are described in the following United States patents: Weissman et. al., Method for Laser Depilation Device and Method, U.S. Pat. No. 4,388,924; Sutton, Depilation Device and Method, U.S. Pat. No. 4,617,926; and Mayer, Depilation by Means of Laser Energy, U.S. Pat. No. 3,538,919. All of these devices and methods teach the removal of hairs one hair at a time with a narrowly focused laser beam. Therefore, they are relatively inefficient and time consuming. A more recent patent by Zaias, U.S. Pat. No. 5,059,192 issued Oct. 22, 1991 discloses a process for using a laser beam matched to the melanin found at the base of the hair follicle and papilla.

What is needed is an improved hair removal process.

SUMMARY OF THE INVENTION

The present invention provides a process for the long term or permanent removal and prevention of growth of unwanted hair. The upper portions of hair ducts (i.e. portions near the skin surface) in a section of skin are contaminated with a contaminant having a high absorption at at least one frequency band of light. The skin is then illuminated with light at the frequency band of high absorption by the contaminant using an illumination process having at least two distinct phases.

In the first of these phases, called the "explosion" or "mechanical" phase, the skin section is illuminated with at least one short pulse of light at sufficiently high power so as to impart sufficient energy in a sufficiently short time period to the contaminant located in upper portions of the hair ducts to cause tiny explosions in the contaminant, forcing portions of the contaminant more deeply into the hair ducts. During the second phase, called the "cooking" or "thermal" phase, the skin section is illuminated with light at a frequency band of high absorption in the contaminant but in a manner chosen to heat the contaminant to a high temperature without substantial explosion or vaporization of the contaminant. The hot contaminant then heats portions of the skin tissue immediately surrounding the contaminant to a temperature high enough and for a long enough period of time to devitalize (kill) the tissue. The process may include a third phase, called the "cleanup" phase, during which the skin section is illuminated with short pulses of light at sufficiently high power so as to impart to the contaminant sufficient energy in sufficiently short time periods to cause additional tiny explosions in and vaporization of portions of the contaminant then remaining in the ducts and additional damage to the skin tissue immediately surrounding the contaminant.

In a preferred embodiment, initially at least some of the hair in the section of skin being treated is removed by waxing so as to allow more space in the hair ducts for infiltration of contaminant. Then the contaminant, such as a mixture of 1 micron graphite particles in mineral oil is applied to the skin surface and massaged to cause some of the contaminant to infiltrate into the hair ducts. During the first phase of illumination, the explosion phase, the skin section is illuminated by a few pulses of a short pulse duration laser beam; e.g., from one to about three Nd:YAG laser pulses at 1.06 micron wavelength, each pulse having an energy density of about 2 Joules per square centimeter ($J/cm^2$) and a pulse duration of about 10 nanoseconds (ns). The photons in this laser beam are scattered greatly by skin tissue but the absorption coefficient of the photons in skin tissue is relatively very small. We estimate that the absorption coefficient for the Nd:YAG photon in the graphite particles is at least several thousand times greater than the absorption coefficient of skin tissue; therefore, substantially all photons encountering a graphite particles in the course of their travel through the skin will be absorbed, the 1 micron carbon particles capturing photons like little "black holes." Because of the high absorption in the graphite particle, the particles are heated very rapidly by one pulse and the pulse duration is so short that very little heat is conducted out of the particle during the pulse. The power density of these pulses is about 200 Megawatts/$cm^2$, enough to heat the particles to their vaporization temperature of about 3,600 degrees C., causing an explosion of the particles and vaporizing a portion (estimated to be about 10 to 30 percent) of the particles. These explosions cause most of the particles on the skin surface to be blown off the skin surface and force many of the particles near the top of the hair ducts deeply into the hair ducts.

During the second illumination phase, the cooking phase, each portion of the skin section is illuminated with 1.06-micron laser light at an energy density of about 2 $J/cm^2$ but with a pulse width of about 100 microseconds. The power density of these pulses is only about 20 Kilowatts/$cm^2$. These pulses impart about the same amount of energy to the graphite particles as the short 10-nanosecond pulses but at a very much slower rate. The particles in turn transfer energy by conduction to the surrounding tissue and oil during the pulse so that the vaporization temperature of the particle is in most cases not reached and there is no significant vaporization or explosion of the particles. In this embodiment the pulses are applied at a 10 Hz rate, but the skin is slowly scanned so that each section is illuminated for only about two to three seconds (about 25 pulses or 50 $J/cm^2$ per scan). The illumination heats up the skin generally (like sunlight or an infrared lamp) in addition to the carbon particles, but the general heating of the skin is at a much slower rate. Thus a scan of a skin section is limited to no more than about 30 pulses and between scans the skin section is allowed to cool. The scan may be repeated as many times as desired because there is no diminution of the quantity of graphite during this phase.

During the third phase of a preferred illumination process, the clean up phase, the skin section is illuminated with about 10 Nd:YAG laser pulses at 1.06 micron wavelength and 10 Hz, each pulse having an energy density as in the first phase of about 2 J/cm² and a pulse width of about 10 nanoseconds. Again, the pulse duration is so short that very little heat is conducted out of the particle during the pulse. As before, the power density of these pulses is about 200 Megawatts/cm², enough to heat the particles to over 3,600 degrees C., cause explosions of the particles and vaporize with each pulse a portion (estimated to be about 10 to 30 percent) of the particles. These explosions cause additional damage to the tissue surrounding the particles and further fragment and distribute the particles in the hair ducts. Also, after about one second of illumination (about 10 pulses) the particles are mostly vaporized or broken into fragments so small that they are invisible to the unaided eye.

In another preferred embodiment, the second phase illumination consists of about 2,000 pulses at 0.2 J/cm² with a pulse duration of 10 nanoseconds. This requires about 200 seconds per skin section but the cross section of the laser beam can be expanded by a factor of ten and the illumination scan time can be increased from about 3 seconds to about 12 seconds or longer without significant risk of general skin burning. At a pulse energy density of illumination of 0.2 J/cm² the particles are heated to temperatures in the range of about 1,000 degrees C.

DETAILED DESCRIPTION OF PREFERRED EMBODIMENTS

Human Skin and Hair

Figure 1:
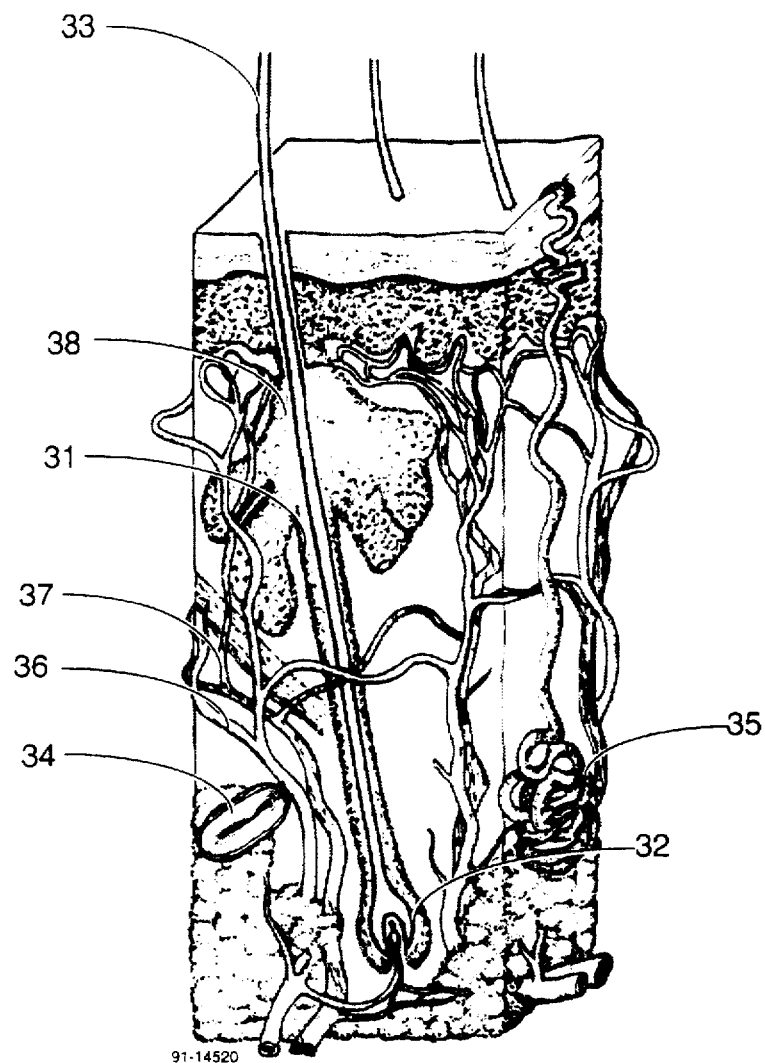
FIG. 1 is a drawing of a section of human skin showing a growing hair.

A section of human skin showing a cross section of one hair is shown in FIG. 1. The FIG. 1 drawing shows a hair shaft 33, a hair duct 31, a nerve ending 34, a sweat gland 35, a sebaceous gland 38 and arteries 36, veins 37, and papilla 32.

Graphite

In the graphite form of elementary carbon, each carbon atom has three near neighbors and a fourth neighbor at a considerably greater distance away, the two lengths being 1.42 Å and 3.42 Å, respectively. (10,000 Angstroms equal 1 micron.) The network of the three nearest neighbors is planar and extends in the two directions of the plane to the boundaries of the solid. The binding forces between the planes are weak and the planes can slip past each other very readily. For this reason, graphite can be used as a lubricating material. Thin layers of graphite can be removed by abrasion and this property is exploited in the ordinary lead pencil in which motion of the graphite rod over paper causes thin layers of the solid to be rubbed off and spread on the paper. For many years laser workers have used paper thinly coated with small particles of graphite to examine the cross section power of certain laser beams. The energy of many laser beams is readily absorbed by the carbon particles and many of the particles react violently, exploding off the paper and leaving "footprints" on the paper representative of the cross sectional power distribution of the laser beam.

Preferred Contaminant

A laser beam absorbing carbon suspension is prepared consisting of graphite powder in mineral oil. The particle size of the powder is preferably about 1 micron and its concentration preferably is about 20 percent by mass. This suspension is used to contaminate the hair ducts, so the suspension is sometimes referred to herein as the "contaminant." The expression "contaminant" is also used to refer to the particles of the suspension, as is apparent from the context.

Cleaning

Figure 2A:
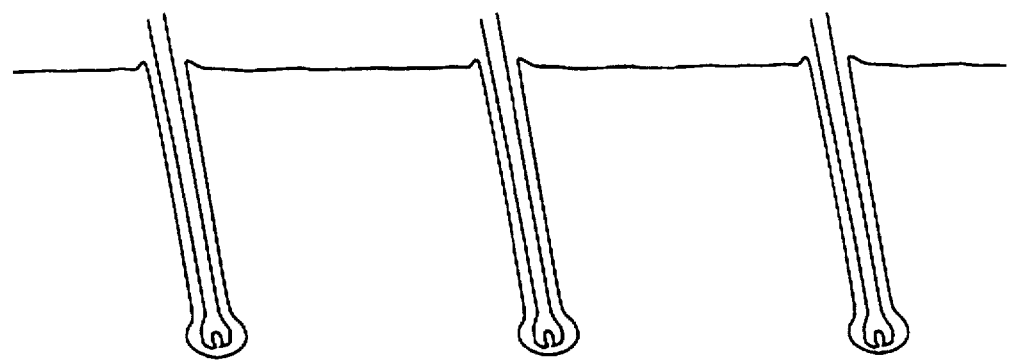
FIGS. 2A, B, C and D show a cross section of skin and 3 hairs during 4 stages of a process of one embodiment of the present invention.

A section of skin with growing hairs is depicted in FIG. 2A. To prepare the skin section for the process of the invention, the skin is preferably washed with soap and water then rinsed with water and dried with a cloth towel. The skin section is then cleaned, as with methyl alcohol, and allowed to dry.

Waxing

The next step in this preferred embodiment is to physically remove the hair shafts from the hair ducts in the skin section to be treated. Preferably this is accomplished using a well known temporary hair removal procedure known as waxing. A suitable wax is the commercially available wax marketed by Select Spa Source of Sausilito, Calif. under the trade name Nature's Own Pine Wax although a wide variety of such waxes are available and would be satisfactory. The hair is removed by following the waxing procedure furnished with the wax.

Figure 2B:
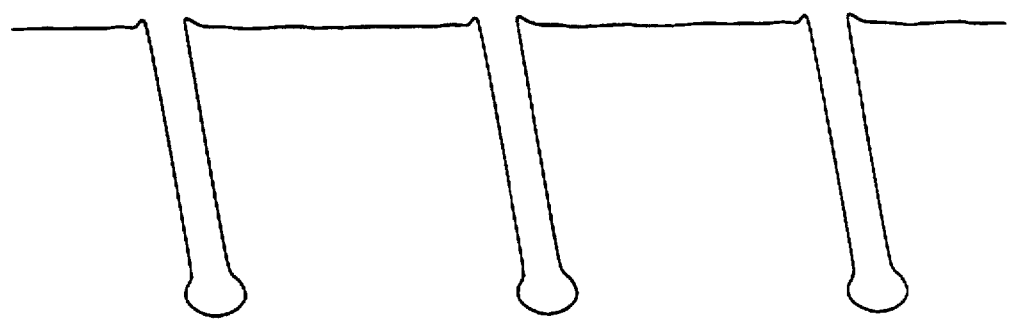

Removal of the hair from the hair ducts greatly increases the space available in the hair duct for the graphite-oil contaminant, permitting a much greater quantity of the contaminant to be infiltrated into the hair duct. FIG. 2B shows the same three hair ducts as FIG. 2A with the hair shafts removed.

Topical Application of Contaminant

Figure 2C:
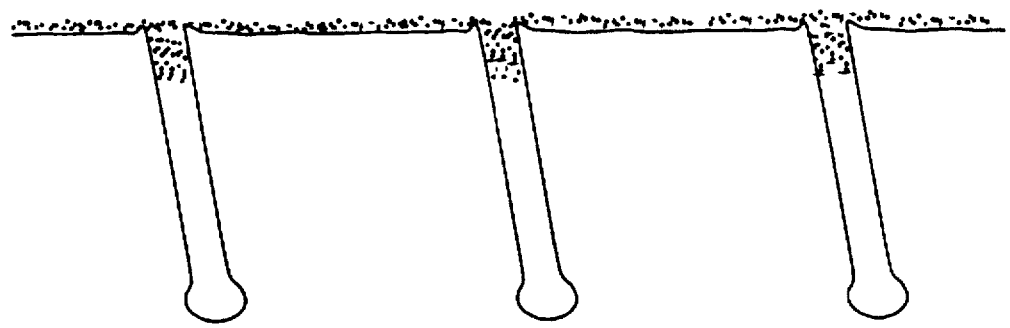

The next step is to apply the graphite-oil contaminant referred to above to the section of skin to be treated. The contaminant is applied to the skin in quantities of about one gram per 10 square centimeters, although the exact amount is not critical. The contaminant is massaged thoroughly on the skin surface for a period of about 1 minute for each 10 square centimeters of skin surface. The principal objective in this step is to cause as much of the graphite particles as feasible to infiltrate into the hair ducts in the skin section. Tests indicate that the graphite oil contaminant can be infiltrated with this massage technique into the hair duct to a depth of about 0.5 mm. For a 100 micron diameter hair duct, this would correspond to about 700,000 carbon particles in the duct. There is great variation in the amount of graphite infiltrated but for purposes of illustration an infiltration of 700,000 one micron particles (about $1.4 \times 10^{-6}$ grams of carbon particles may be assumed.) At the conclusion of the massaging step, the contaminant is present in the upper part of the hair duct, and the skin surface is substantially covered with graphite-oil contaminant as shown in FIG. 2C.

Phases of Illumination

As indicated above, the present invention includes at least two distinct phases of illumination with the objective of achieving maximum hair destruction with minimal damage to skin tissue. In a preferred process the illumination is provided by a Nd:YAG pulsed laser operating at a wavelength of 1.06 microns with a beam cross sectional area of about 0.5 cm². Controls on the laser permit selection of short pulses of 10 ns duration using a Q switch and a long pulse duration of about 100 microseconds (100,000 ns), with the Q switch disconnected. (The pulse duration is approximately the interval of time over which the pulses are at at least one half maximum power.) Pulse energy can be adjusted to between about 0.1 J and 1.25 J, corresponding to 0.2 J/cm² and 2.5 J/cm² for the 0.5 cm² beam.

Explosion Phase

As stated above, the first phase of the illumination process is referred to as the "explosion" phase. The laser is adjusted to produce 1 Joule per pulse which is equivalent to about 2 J/cm² since the beam cross section is about 0.5 cm². The pulse duration is 10 ns and the repetition rate is 10 Hz. Each portion of the skin section to be treated is illuminated with about two to three pulses. This is done by scanning the 0.5 cm² 10 Hz beam over the skin surface at the rate of about 2 cm/s.

Each pulse contains about $1 \times 10^{19}$ photons. The 1 micron graphite particles are very highly absorptive of the 1.06-micron laser photons. The absorption coefficient of graphite is estimated to be between several thousand to about 100 thousand times greater than the absorption coefficient for typical skin tissue. The penetration depth for 1.06 micron photons in graphite is substantially less than 1 micron so substantially all photons encountering a particle are absorbed by it. The 1.06-micron photons are well scattered by skin tissue. The scatter coefficient for dermal tissue is estimated to be about 100 cm$^{-1}$ whereas the absorption coefficient is estimated to be about 0.33 cm$^{-1}$. Therefore, the length of the path traveled by photons between scatters is estimated to be about 100 microns and the path traveled in the dermis before absorption in the dermal tissue is estimated to be 3 cm. The result of the large scattering is that the 1.06-micron photon flux builds up and is actually greater (by a factor of about 5) just below the surface of the skin than the incident flux on the surface of the skin. At two to three mm below the surface (about the depth of most hair roots) the flux has decreased but is still about equal to or maybe a little less than the incident flux. Almost all of the photons entering the skin surface are ultimately absorbed in the carbon or absorbed in the skin tissue.

The cross sectional area of a 1 micron particle is roughly $1 \times 10^{-8}$ cm² so the energy absorbed by a typical particle out of a 2 J/cm² flux is in the range of about $2 \times 10^{-8}$ J. This is a very small amount of energy but the particle is also very small (with a volume of about $1 \times 10^{-12}$ cm³). Its density is about 2 gm/cm³ and its average specific heat is about 2 J/gmC over the temperature range from ambient up to its vaporization temperature. Therefore, each pulse pumps enough energy into the graphite particle to raise its temperature by approximately:

$$\Delta T = \frac{Q}{mc} = \frac{2 \times 10^{-8} J}{(2 \times 10^{-12} gm)(2 J/gm\ °C.)} = 5,000°\ C.$$

However, graphite vaporizes at about 3,600° C. Thus, only a portion of the energy absorbed by the particle is used to heat it from 27° C. (normal skin temperature) to its vaporization temperature. The remainder of the absorbed energy is released in a miniature violent explosion of the particle in which a portion of the particle is vaporized and the particle is broken into smaller particles which recoil away from the explosion site. The explosion also creates a shock or pressure wave which pushes other particles away from the explosion site. The heat capacity of carbon averages about 2 J/gm°C. over the range 0 to 3,600° C. The heat content to raise the temperature of graphite to the vaporization point is then about 7,200 J/gm. Thus, in the above example (7,200 J/gm)×($2 \times 10^{-12}$ gm)=$1.4 \times 10^{-8}$ J of the absorbed laser energy is used to raise the temperature to the vaporization level. The remaining $0.6 \times 10^{-8}$ J absorbed causes the vaporization of a portion of the graphite particles. The heat of vaporization of carbon is about $6 \times 10^4$ J/gm; therefore, the energy needed to vaporize all of the 1 micron ($2 \times 10^{-12}$ gm) particle is about $12 \times 10^{-8}$ J. Hence, in this illustration only about 5 percent of the particle is vaporized with each pulse.

Figure 2D:
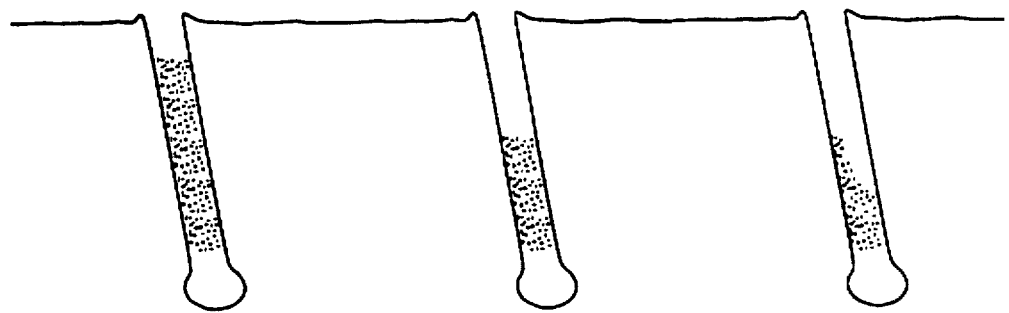

One effect of the miniature violent explosions is to blow essentially all of the particles off the surface of the skin. Also, some of the particles and portions of particles in the upper parts of the hair ducts are blown out of the hair ducts. Most of the particles in the upper portion of the hair ducts, however, are shielded to some extent by particles surrounding them and are forced further down the ducts by the explosion of particles near the top of the ducts. FIG. 2D shows some typical distribution of graphite particles in the ducts after the conclusion of the explosion phase. If it is assumed that the quantity of graphite in the typical duct is roughly $1.4 \times 10^{-6}$ gm (700,000 particles) and at an average of $2 \times 10^{-8}$ J is absorbed per particle per pulse, then the energy absorbed in a hair duct is about $14 \times 10^{-3}$ J/pulse. This is equivalent to the amount of energy needed to increase the temperature of a cylinder of water 3 mm long and about 67 microns in diameter by 80 degrees C. The estimate would be much higher if greater quantities of particles were present and if flux buildup near the skin surface were taken into account. Skin tissue has a specific heat which is about the same as water. From this illustration it is expected that some damage occurs to skin tissues within a few microns of the upper part of the hair duct during the explosion phase but probably not enough to devitalize the hair. Also, some damage may result from the shockwaves or pressure waves. However, the main advantage of the explosion phase is that particles are forced down the duct to the region of the duct near the papilla through which growing hair receives its nourishment. The explosion phase also clears substantially all particles off the surface of the skin.

Cooking Phase

The second phase of the illumination phase is referred to as the "cooking" or "thermal" phase because the objective of this phase is to heat the skin tissue adjacent to the hair duct to a temperature high enough to permanently devitalize (kill) it, so that the tissue cannot support future hair regrowth. Prior to starting this phase, graphite particles remaining on the skin surface are cleaned off as completely as feasible with a cloth soaked in mineral oil. This also tends to fill in void spaces in the hair duct (especially at the top of the duct) with mineral oil, which transmits 1.06 microns light very well. During the cooking phase a volume within about 150 microns radius of the center of the hair duct is targeted, and heating is done primarily by applying heat from laser illumination to the graphite particles which are now distributed deeply in the hair duct. Laser photons absorbed in the graphite particles include photons scattered into the hair duct from the surrounding skin tissue and also photons transmitted down the hair duct through mineral oil which now fills the upper part of the duct. Heat is transferred by conduction from the graphite to the surrounding tissue. During the "cooking" phase heat energy is applied slowly enough so that substantial vaporization or fracturing of the graphite is avoided, and thus heat may be applied to the tissue via the graphite particles a very large number of times. In one preferred embodiment, for the cooking phase, the Q switch is disconnected so that the laser produces pulses of about 100 microseconds duration. Energy density may be 2 J/cm$^2$ and the repetition rate set at 10 Hz.

The skin is scanned so that each portion of the section of the skin being treated is illuminated for only about 2.5 seconds (about 25 pulses) before being allowed to cool down e.g., for about 60 seconds. Each pulse, in addition to heating the graphite, applies heat generally to the skin tissue and increases the temperature of the skin tissue about 0.5 to 1.5 degrees C., so more than 30 pulses could cause the skin portion being illuminated to become very warm. Experiments have indicated that burning pain is experienced after five to seven seconds of 2 J/cm$^2$ 10 Hz pulses (100 to 140 Joules/cm$^2$); therefore, the number of laser pulses between "cool down" periods is preferably limited to well below this threshold.

Each portion of the skin section being treated receives about 20 scans for a total of about 500 pulses. (This takes a total of about 50 seconds per portion.) Each 1 micron particle absorbs very roughly about $2 \times 10^{-8}$ joules per pulse or about $50 \times 10^{-8}$ joules per 2.5 second scan. Heat diffuses out from the graphite particles to a distance of about a few tens of microns during the first few milliseconds after the start of a scan and diffuses a few hundred microns in one second. If it is assumed that the equivalent of 500,000 one micron cubic particles are present per duct, each duct would receive roughly about 0.25 Joule per each 2.5 second scan. This 0.25 Joule would be sufficient to increase the temperature of a volume of water 3 mm long and 563 microns diameter by 80 degrees C. The specific heat of skin tissue is about the same as that of water. Skin tissue is devitalized (killed) if kept at a temperature of 70 degrees C. for about 1 second. Skin tissue closest to the carbon particles will be heated to temperatures much higher than 70° C. It is estimated that skin tissue within about 1 to 3 hair diameters of the hair ducts is devitalized during this phase. Actual biopsy studies of both pig and human skin confirm these estimates.

Clean-Up Phase

Preferably during a third phase of the illumination process, which is referred to as the "clean up" phase, the skin section is illuminated with about ten Nd:YAG laser pulses at 1.06 micron wavelength and 10 Hz, each pulse having an energy density as in the first phase of about 2 Joules/cm$^2$ and a pulse width of about 10 nanoseconds. Again, the pulse duration is so quick that very little heat is conducted out of the particles during the pulse. As before, the power density of these pulses is about 200 Megawatts/cm$^2$, enough to heat the particles to over 3,600 degrees C., cause explosions of the particles, and vaporize with each pulse a portion (about 5 percent) of the particles. These explosions cause additional damage to the tissue surrounding the particles. Also, after about 10 to 30 pulses, the particles are mostly vaporized or broken into particles so small that they are invisible to the unaided eye.

EXPERIMENT WITH SMALL PARTICLES

In order to confirm the above description, experiments were conducted in which these small carbon particles were irradiated with pulses of the type described above.

Particles in a Bottle

A small number (about 0.1 gm) of one micron size graphite particles were placed in an enclosed glass vial in an air atmosphere and irradiated with pulses as described above under the "Explosion Phases" with no scanning. The particles were continuously broken into smaller and smaller particles and after about 10–15 pulses they vanished. It is believed that the very small particles were oxidized to form CO or $CO_2$. When the same experiment was conducted in an argon atmosphere the particles continued to break into smaller and smaller parts until they were nearly invisible to the unaided eye (i.e. about 0.1 micron to 0.05 micron).

Experiment with Fiber Optic Tube Simulating Hair Duct

Laboratory experiments were also conducted to demonstrate the effectiveness of the explosion phase and the cooking of the preferred process. In one experiment carbon-oil contaminant was infiltrated into the top of a 100 micron inside diameter, 5 mm long fiber optic tube to a depth of about 1 mm. The bottom of the tube was blocked and the top of the tube was irradiated with one 10 ns pulse from a 1.06 micron wavelength Nd:YAG laser at 2 J/cm$^2$. As a result of miniature particle explosions at the top of the tube, graphite particles were distributed throughout the tube with maximum concentration of particles at the bottom of the tube. The tube with 100 microsecond 2 J/cm$^2$ pulses for five seconds. The heat absorbed by the carbon caused the inner surface of the tube and tube's fiber clad to deform. A tube without graphite was illuminated with 2 J/cm$^2$ for 25 seconds with no visible effect on the tube. In another test of a tube with graphite in it and illumination at 3 J/cm$^2$ for five seconds, the tube melted.

Pig Experiment

In other experiments the preferred process was tested with pig skin in vitro. In one experiment to examine the explosion phase of the preferred illumination process, hairs in sections of the pig skin was removed prior to the topical application of the contaminant and in other skin sections the hair were not removed. After the topical application of the contaminant, the skin sections were illuminated with 1, 2, 5 and 10 pulses (all at 10 ns duration) at power levels of 1 J/cm$^2$, 2 J/cm$^2$ and 3 J/cm$^2$. The skin was then biopsied to permit examination of the follicles. The maximum and deepest contamination was produced with 2 pulses at 2 J/cm$^2$. At 3 J/cm$^2$ vaporization of the carbon became substantial. In those sections where the hair was removed the graphite particles completely filled the hair ducts with heavy concentration at the bottom of the duct. In those sections where the hair was not removed, the graphite particles were distributed deeply into the duct, but generally very few particles reached the bottom of the ducts.

Hair in Egg White Experiments

Short-Pulse-High Power

Figure 4A:
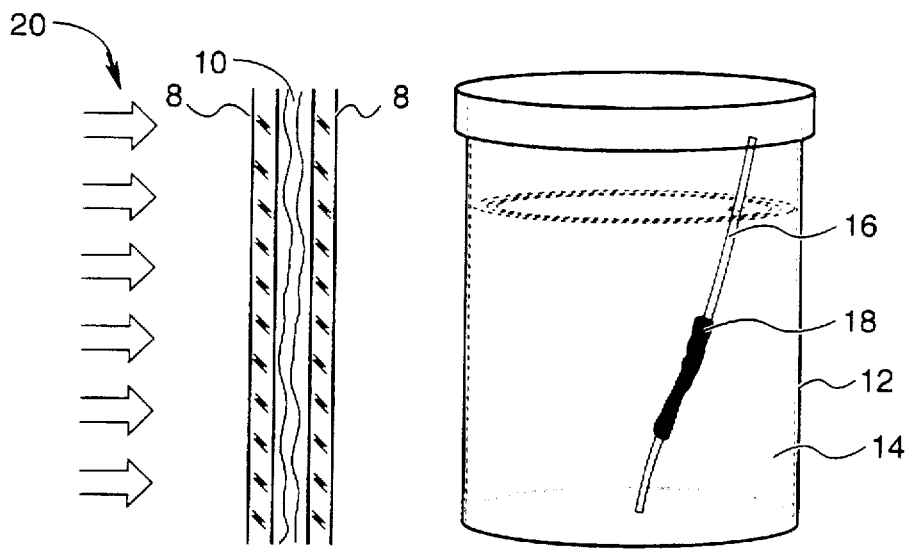
FIG. 4 A through C shows an experiment with turkey skin, egg white, a partially contaminated hair and a laser beam to demonstrate some of the elements of the present invention.
Figure 4B:
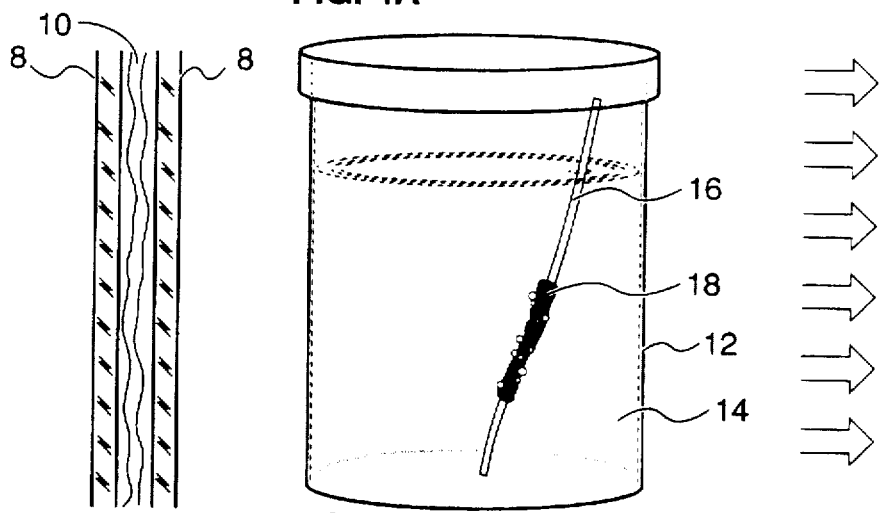
Figure 4C:
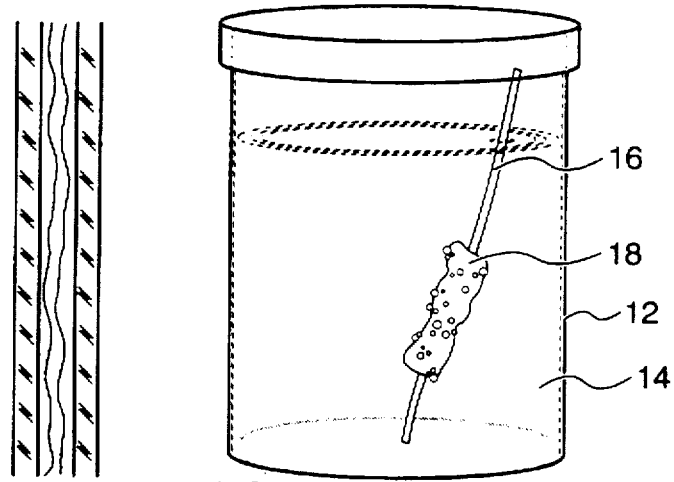

FIGS. 4A, 4B and 4C are sketches illustrating an experiment performed in order to demonstrate elements of this hair removal process. Three layers of turkey drumstick skin 10 were sandwiched between two glass microscopic slides 8. The thickness of the 3 layers of turkey skin was about 2 millimeters (approximate depth below the skin surface of the bottom of human hairs). A single human hair 16 about 10 cm long was coated over a 3 cm section with a mixture 18 of 1 micron particles of carbon (graphite) and mineral oil (about equal mass). The hair was immersed in chicken egg white 14 contained in a small (5 cm diameter) vial 12. The drawing is roughly to scale except the diameter of the hair and the carbon-oil contaminant is exaggerated.

The hair including the coated section was illuminated with 100 pulses of laser radiation from a Nd:YAG laser.

The following is a description of the pulsed laser beam:

| | |
|---|---|
| Wavelength | 1.06 micron |
| Energy per pulse | 1.5 Joules |
| Beam area | ½ cm² |
| Energy density | 3 J/cm² |
| Frequency | 10 pulses per second |
| Pulse duration | 10 ns |

Each pulse 20 passed through the slides and turkey skin with no apparent effect on the skin. The beam also passed through the wall of the vial and through the egg white.

The beam was scanned over the hair so that each portion of the hair received about 5 pulses. The beam had no effect on the hair or the egg white except near the section of the hair which was coated. In that section, the carbon in the mixture absorbed sufficient energy from the beam to cook the egg white immediately surrounding the coated section of the hair. In this experiment the cooking process could be readily observed because uncooked egg white is transparent.

FIG. 4B shows the result of the first 10 pulses of beam 20 (about 3 pulses into the carbon) passing through the elements of this experiment. The only discernible effect of these pulses was an obvious heating and cooking of the egg white immediately adjacent to the coated section of the hair. Some fragments of carbon particles were thrown off the hair but were trapped in the immediate surrounding egg white. These fragments were further fragmented by subsequent pulses into very small fragments or oxidized. FIG. 4C shows the results of 100 pulses. The egg white tissue in the immediate vicinity of the coated section was cooked to a thickness of about 500 microns. There was no damage discernible in either the turkey skin or anywhere else in the egg white or to the hair itself other than the coated section. These conclusions apparent to the unaided eye were checked and confirmed under a microscope. Only a very few small particles of carbon remained.

Long Pulse-High Energy

Figure 5A:
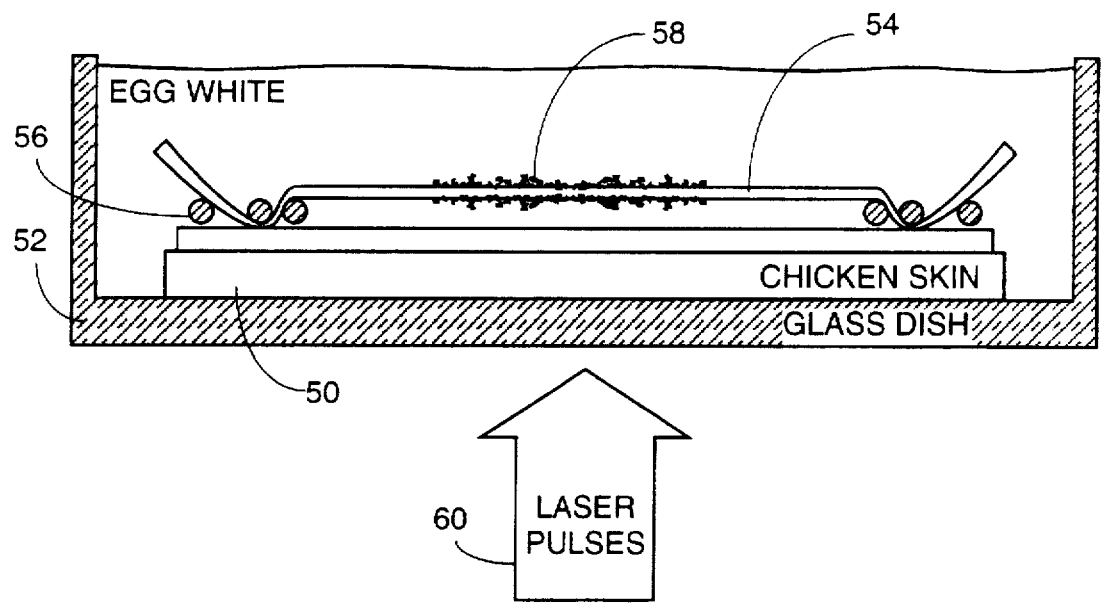
FIGS. 5A and 5B show another experimental set up to demonstrate elements of the present invention.
Figure 5B:
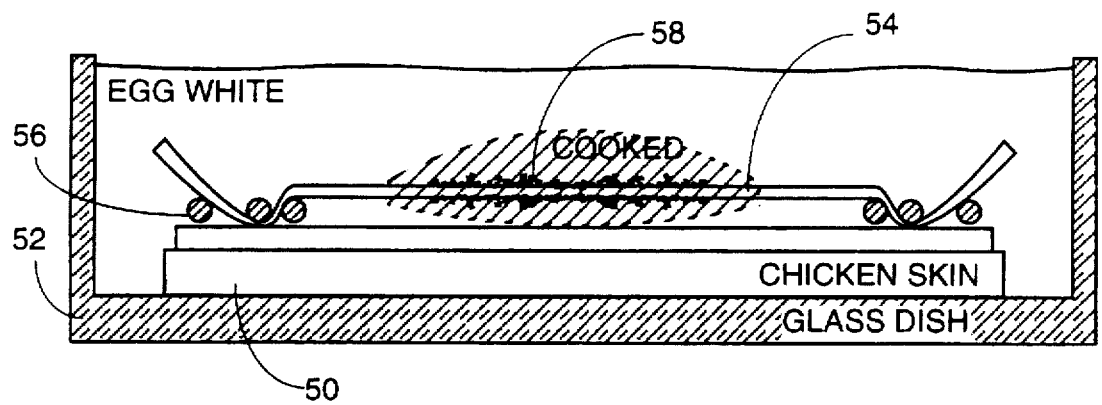

FIG. 5A shows a drawing of another egg white experiment conducted to test the cooking phase. Two layers of chicken skin 50 were placed at the bottom of a glass dish 52. Separate ends of a human hair 54 was glued with super glue to paper clips 56 and the portion of the hairs between the clips were coated with a preferred graphite-oil contaminant 58 (about equal mass of mineral oil and 1 micron graphite particles). The hair-paper clip assembly was placed on the chicken skin and the hair, paper clips and skin were covered with egg white. The hair was then illuminated from below through the chicken skin and the egg white with 100 microsecond laser pulses 60 at 2 J/cm² at the rate of 10 Hz for about 2 to 3 seconds. This process was repeated several times allowing for cooling between illuminations. With this setup, the experimenter could watch the hot graphite cook the adjacent egg white, and the hair, particles and egg white could be viewed periodically with a microscope. Egg white immediately surrounding the contaminant coated hair was cooked with no damage to the skin or any egg white not close to the contaminant. Also, after many repeat illumination periods of about 2.5 seconds (during which about 50 J/cm² was delivered), there was no detectable diminution of the carbon particles. Therefore, it was concluded that the "cooking" process (with in-between cooling periods) could have continued indefinitely with no apparent damage to the skin or egg white except the egg white in the immediate vicinity of the contaminant.

Short Pulse-Lower Energy

The above experiment was also conducted as described above but with pulses at 0.2 J/cm² with the Q switch in place so that the pulse was 10 ns and 0.2 J/cm². There was cooking of the egg white adjacent to the graphite but no violent explosion or obvious fragmentation of carbon particles. And at the conclusion of a large number of pulses there was no substantial diminution of the graphite particles. (At 0.2 J/cm² about 250 pulses could be applied before general skin heating would become a problem, and a pulse frequency to 50 or 100 Hz is recommended.) A rough estimate the temperature rise in the carbon particles is obtained as follows:

$$\Delta T = \frac{\phi}{mc} = \frac{0.2 \times 10^{-8} \text{ J}}{(2 \times 10^{-12} \text{ gm})(1 \text{ J/gm °C.})} = 1,000° \text{ C.}$$

This is based on an estimated particle cross section of $1 \times 10^{-8}$ cm², mass of $2 \times 10^{-12}$ gm and a specific heat of about 1 J/gm°C. in the temperature range between ambient and 1,000° C.

Experimental Conclusion

These experiments show that, when illuminated with 10 ns pulses and 2 J/cm² energy, carbon particles explode violently (on a miniature scale) and are partially vaporized. However, increasing the pulse duration to 100 microseconds (with pulse energy at 2 J/cm²) or reducing the energy to about 0.2 J/cm² (with a 10 ns pulse) permits delivery of sufficient heat to the carbon to cook tissue with no substantial vaporization or explosion of the carbon. This permits the "cooking" phase to be continued indefinitely.

OTHER PREFERRED EMBODIMENT

Buckey Balls

Another potential method of increasing the quantity of contaminant in the hair duct is to use very small spherical particles. A carbon molecule meeting these specification has recently been produced and is available commercially. These molecules are known as "Buckey balls" or $C_{60}$. Buckey balls are carbon molecules, roughly spherical, each consisting of 60 atoms of carbon. Buckey balls are commercially available, (e.g., under the name Buckminsterfullerene from Sigma Chemical Company of St. Louis, Mo.) at prices of about $300 per gram. An initial experiment with this form of carbon contaminant indicates very potentially promising results. The Buckey balls are very absorptive of Nd:YAG laser beams and appear to infiltrate into hair ducts very readily.

Chemical Explosives

The explosives and/or cleanup phases of the various embodiments of this invention could be enhanced by utilizing a contaminant that will chemically react exothermically upon absorption of the short pulses of light. For example, small quantities of a mixture of 75% potassium nitrate ($KNO_3$) 15% carbon (c) and 75% sulfur (s), commonly known as black powder, explodes violently when illuminated with the 2 $J/cm^2$ Nd:YAG laser pulse. The energy released (in the form of heat and mechanical energy) is estimated to be 10 to 30 times that released from an equal quantity of graphite powder illuminated with the same laser beam. The black powder can be provided in powder form with sizes small enough to infiltrate the hair ducts and the powder can (like the graphite powder) can be mixed with mineral oil for topical application to the skin.

Black powder or another absorptive/chemically reactive material may also be used as part of the contaminant initially applied to the skin—i.e., such contaminant may be a mixture of black powder and the graphite/oil suspension described herein. Explosions of the black powder of this contaminant (and of portions of the graphite) during the explosion phase may help force the remaining graphite to the bottom of the hair ducts, with such remaining graphite then being available for absorption of laser energy and heating of tissue during the cooking phase.

There are a vast number of other well known explosive materials which release energy exothermically and can be ignited with short pulses of light which penetrate skin tissue.

Double Application of Contaminant

Another preferred method of increasing the quantity of contaminant in hair ducts is to repeat the topical application and explosion phase one or more times. Experiments have indicated that the explosion phase opens the ducts slightly wider providing more room for contaminant on the second application. Increasing the quantity of graphite in a duct increases the amount of heat which can be imported to the duct during the cooking phase. Steps in one variation of this method would include the following steps:

1. waxing
2. first topical application of contaminant
3. first explosion phase
4. first cooking phase
5. second topical application
6. second explosion phase
7. second cooking phase
8. clean up phase For difficult hair removal cases steps 5, 6, and 7 could be repeated several times. On each repetition, additional graphite would accumulate in the hair duct, permitting more and more heat to be imported during the cooking phase. Another approach is the same steps as listed above with the first cooking phase (step 4) omitted. The cleanup phase removes substantially all graphite from the duct or fractures it into particles of very small sizes.

Mineral Oil Path to the Papilla

Figure 6:
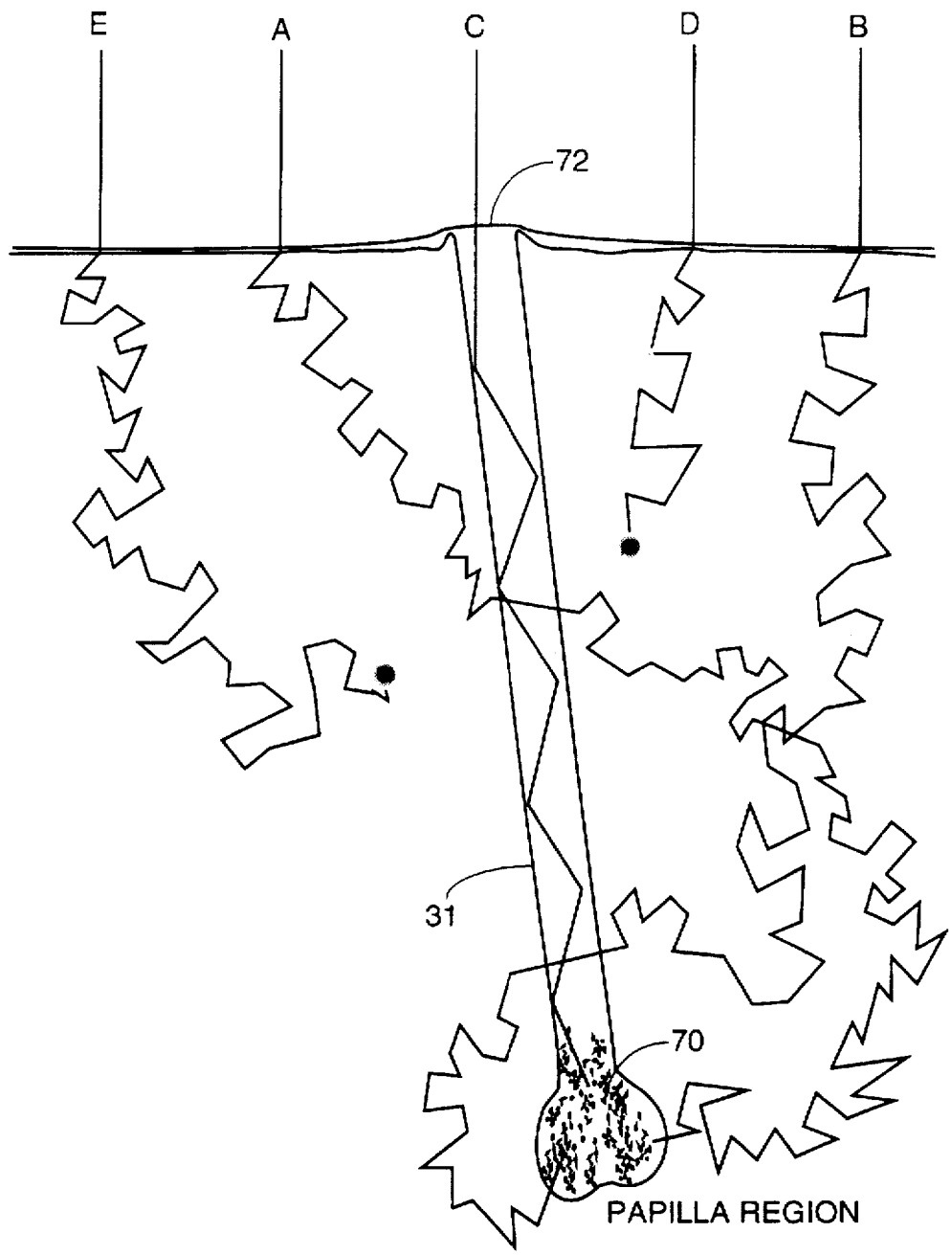
FIG. 6 illustrates a preferred embodiment with fluid providing a photon pathway through hair ducts to the papilla region.

In another preferred embodiment of the present invention, graphite particles are deposited in the hair duct as close to the papilla as possible and the remainder of the hair duct is filled with mineral oil. A cooking phase is then used to provide maximum preferential heating of tissue in the papilla region of the hair duct. Steps in one variation of this method would include the following:

1. waxing
2. topical application of contaminant
3. first explosion phase
4. clean skin surface with mineral oil
5. apply mineral oil to skin surface and massage into ducts
6. cooking phase
7. clean up phase Experiments conducted on mineral oil indicate that such oil, which is transparent to the 1.06 micron light and has an index of refraction substantially greater than that for skin, will conduct light beams down the hair duct to the papilla area. Absorbers in the papilla region would then receive illumination both from photons scattered from the dermis and photons traveling through the mineral oil in the upper region of the hair duct. This effect is illustrated in FIG. 6, which shows the paths of five typical photons A, B, C, D and E. A and B are scattered many times in the dermis and are ultimately absorbed in graphite particles 70 in the bottom of the hair duct 31. Photon C travels down the hair duct through the mineral oil 72 similar to photons in an optical fiber and also is absorbed in graphite particles at the bottom of the hair duct. Photons D and E are depicted as being absorbed in skin tissue.

Another approach would consist of the following steps:

1. waxing
2. topical application of lotion
3. first explosion phase
4. clean skin surface with mineral oil
5. apply mineral oil to skin surface and massage into ducts
6. first cooking phase
7. second explosion phase
8. repeat step 5
9. second cooking phase
10. clean up phase Steps 6 and 7 help clean out and open up the upper portions of the hair duct to permit a cleaner and wider passage for photons through the mineral oil in the hair duct.

VARIATIONS

Persons skilled in the laser-medicine art will recognize that many other light source-contaminant combinations could be used to practice this invention. The important attributes of the combinations are:

1) The light source must penetrate skin tissue, at least for the cooking phase.
2) The contaminant should be capable of being infiltrated in significant quantities into the hair ducts.
3) The contaminant must be very highly absorptive of energy at the wavelength of the beam and capable of being forced deeper into the hair ducts (as by explosion) upon illumination with short high power pulses.
4) The process includes at least two distinct phases: a) an explosion phase to distribute the particles in the hair ducts and b) a cooking step during which heat energy is applied via the contaminant without substantial fragmentation or vaporization of the contaminant.

In addition, a clean up phase is highly desirable in which contaminant remaining in the duct after the cooking phase is vaporized by short pulses of light.

Preferably the contaminant (e.g., graphite) vaporizes at a very high temperature and during the illumination period of the explosion phase absorbs enough energy to partially vaporize. These circumstances permit the contaminant to transfer high temperature heat to skin tissue and also to provide an explosive force to distribute light absorbing contaminant to the bottom of the hair duct. Ultimate vaporization and breaking into small parts of the contaminant during the clean up phase also serves the useful function of removing most of the contaminant from the duct during the treatment process. Fracturing the contaminant into ever smaller particles is also a satisfactory process of effectively removing the particles. This is because small particles become invisible after a few fractures and once they are reduced to a small fraction of a micron the body's immune system can remove them.

Although particle size is not critical, the particles must be small enough to infiltrate the hair ducts and they should be large enough to absorb the photons. Preferred sizes are preferably in the range of 0.5 microns to about 5 microns.

With illumination that penetrates skin tissue about 0.5 cm, no more than about 60 J/cm$^2$ can be added without general overheating of the skin tissue unless a portion of the heat is dissipated. This overheating can be avoided by applying the heat in increments allowing the skin to cool naturally between illuminations. Another approach is to artificially cool the surface of the skin either prior or during the illumination or both prior to and during the illumination. Tests have been using cold air, ice and canned nitrogen to cool the surface of the skin. However, use of topical cooling is recommended only when natural cooling is not effective since cooling the surface of the skin may interfere with nerve sensors in the skin which provide a natural alarm function to prevent unintended damage to the skin.

Many contaminants other than graphite particles in mineral oil may be used. Tests have been conducted using acrylic tattoo inks which have been approved by the FDA for tattoo use. Black and blue tattoo inks marketed by Spaulding and Rogers appear to work well with a Nd:YAG laser operating at 1 Hz, 1.06 micron with an energy density of about 3 J/cm$^2$. Less success has been achieved with inks of other colors.

Figure 3A:
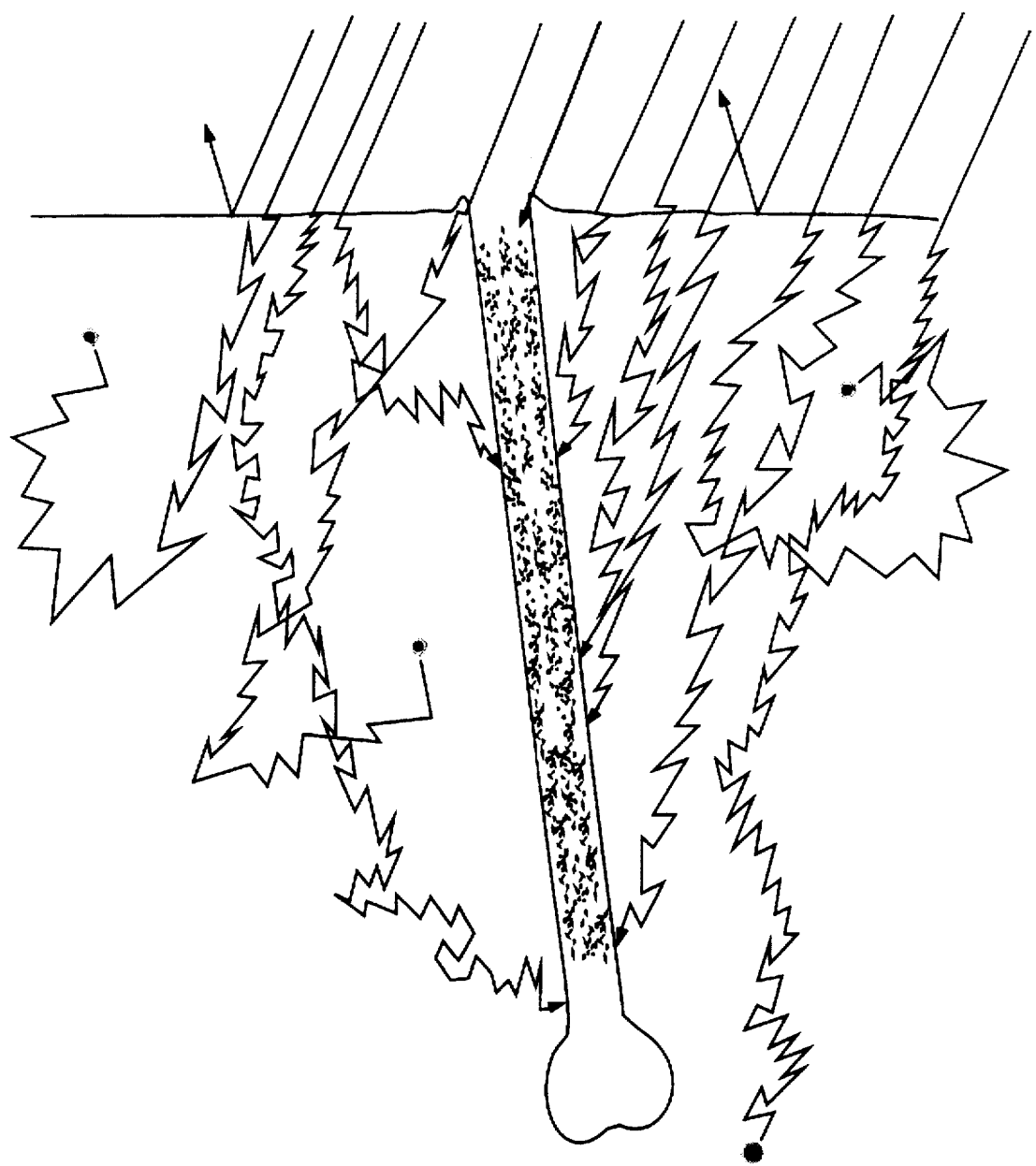
FIGS. 3A and 3B shows qualitatively the paths of the photons of a laser pulse showing absorption in a carbon-oil suspension.
Figure 3B:
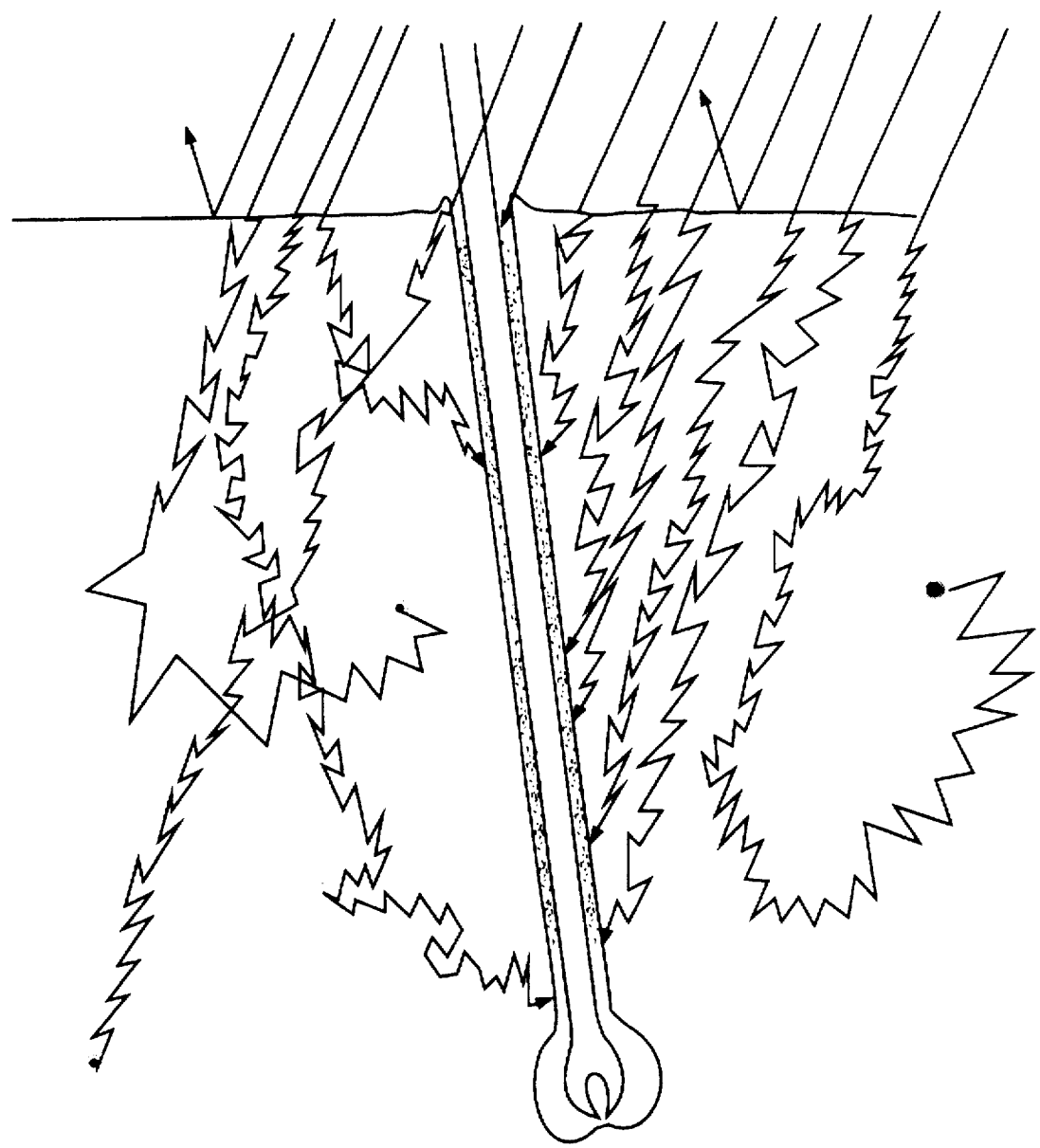

It is not necessary to remove the hairs prior to illumination. FIG. 3B depicts an illumination phase with the hair shaft remaining in the duct as compared to FIG. 3A where the hair has been removed. The three preferred illumination phases are as described above. The results are usually not as good with the hair in place during the process since the quantity of graphite which can be loaded into the duct is greatly reduced.

Pulse durations other than those described above may be used. For example, preliminary tests have been performed with 2 ns pulses for the explosion phase. These pulses appear to provide greater explosions but it may be necessary to reduce the energy per pulse to avoid general damage to skin tissue.

We have discovered that better transmission through the skin can be achieved by stretching the skin. This also helps keep the ducts open which is important when utilizing the embodiment in which photons are transmitted down the hair duct through mineral oil. Pressing the skin can reduce the distance between the skin surface and the hair root and may thereby result in more photons being absorbed in the lower regions of the duct.

Illumination during the cooking phase can be effected by any of a wide variety of illumination sources, and with different pulses, from very short nanosecond pulses to much longer pulses, or even a continuous beam for periods of a few seconds. The objective is to impart as much energy as feasible to the graphite particles without causing general overheating of skin tissue. The laser could be controlled with a microprocessor to automatically provide a Q-switched beam, then a non-Q-switched beam followed by a Q-switched beam. Such a system could be useful in conjunction with automated scanning.

Another embodiment of this invention is to utilize for the cooking phase a laser pulse which vaporizes a very small percentage (such as 1%) of the graphite in the duct with each pulse. This would permit several hundred pulses before the quantity of graphite is reduced to the point of ineffectiveness. At that point a few 2 J/cm$^2$ pulses could be applied to vaporize most of the remainder.

The above-described methods are exemplifications of preferred embodiments of the inventions and many other possible variations are within its scope. The invention is to be measured by the appended claims and their legal equivalents, and not limited to or by the examples which have been given.

What is claimed is:

1. A process for the long term prevention of growth of hair in hair ducts on a section of human skin comprising the steps of:
   (a) applying to said skin section a contaminant having a high absorption at at least one frequency band of light, and having a propensity to explode upon exposure to short high energy pulses of said light, said application being performed in a manner so as to assure that at least a portion of said contaminant infiltrates said hair ducts.
   (b) illuminating in a first illumination phase said skin section with a plurality of the short high energy pulses of said light at a frequency band of high absorption by said contaminant, thereby causing explosions in said contaminant so as to spread said contaminant in said hair ducts, and
   (c) illuminating in a second illumination phase said skin section with light at a frequency band of high absorption by said contaminant, said light devitalizing skin tissue adjacent to said contaminant substantially without vaporizing or fragmenting said contaminant.

2. A process as in claim 1 and further comprising illuminating said skin in a third illumination phase with a plurality of short pulses of light at at least one frequency band of high absorption by said contaminant, said short pulses causing explosions in and vaporization of at least a substantial portion of said contaminant remaining in said hair ducts.

3. A process as in claim 2 wherein steps (a), (b) and (c) are repeated at least once prior to performing said third illumination phase.

4. A process as in claim 1 wherein said short pulses of light are provided by a Nd:YAG laser operating at a wavelength of about 1.06 microns.

5. A process as in claim 1 wherein said contaminant comprises a very large number of small particles which vaporize or fragment upon exposure to said short high energy pulses of said light.

6. A process as in claim 5 wherein a large portion of said small particles are small enough to penetrate said hair duct but larger than 1 micron.

7. A process as in claim 5 wherein a large portion of said small particles are small enough to penetrate said hair duct but larger than 0.5 micron.

8. A process as in claim 5 wherein said particles are graphite particles.

9. A process as in claim 8 wherein the energy delivered during said second illumination phase is delivered in laser pulses of about 10 nanoseconds duration with an energy density of about 0.2 J/cm$^2$.

10. A process as in claim 5 wherein the duration of said short high energy pulses measured at one half maximum power of the pulses is no longer than 50 nanoseconds.

11. A process as in claim 1 wherein said second illumination phase comprises a plurality of separate illuminations, during which said skin section is heated up, separated by time periods during which said skin section is permitted to cool down.

12. A process as in claim 1 wherein the energy delivered during said second illumination phase is delivered in laser pulses of about 100 microseconds duration.

13. A process as in claim 1 wherein said contaminant comprises $C_{60}$ carbon molecules known as Buckey balls.

14. A process as in claim 1 and further comprising the step of removing at least a portion of said plurality of said hairs from within said hair ducts prior to applying said contaminant.

15. A process as in claim 14 wherein said at least a portion of said hairs are removed by waxing.

16. A process as in claim 1 wherein steps (a), (b), and (c) are repeated at least once.

17. A process as in claim 1 wherein steps (a) and (b) are repeated at least once prior to step (c).

18. A process as in claim 1 and further comprising an additional step between steps (b) and (c) of applying to said skin section a fluid transparent to light at said frequency band of high absorption, said application being performed in a manner so as to assure that at least a portion of said fluid infiltrates said hair duct.

19. A process as in claim 18 wherein said fluid has an index of refraction which is greater than the index of refraction of said skin.

20. A process for the long-term prevention of growth of hair in hair ducts on a section of human skin comprising the steps of:
  (a) applying to said hairs and skin section a contaminant comprising a very large number of small carbon particles, said application being performed in a manner so as to assure that at least a portion of said contaminant infiltrates into said hair ducts.
  (b) illuminating said skin section with at least one short pulse of light which is readily absorbed in carbon, said at least one short pulse having sufficient energy to cause a large number of said carbon particles to explode into two or more fragments so as to spread said contaminant in said hair ducts.
  (c) illuminating said skin section with light at a frequency band of high absorption by said carbon particles, said light devitalizing skin tissue adjacent to said contaminant, substantially without vaporizing or fragmenting the carbon particles.

21. A process as in claim 20 wherein said at least one short pulse of light is a plurality of short pulses of said light at at least one frequency band of high absorption by said contaminant, said plurality of said short pulses of said light causing a large number of explosions in and vaporization of said contaminant.

22. A process as in claim 21 wherein said illumination steps (b) and (c) are repeated until substantially all the fragments are smaller than 0.05 microns.

23. A process as in claim 20 wherein a large portion of said small particles are small enough to penetrate said hair ducts but larger than 0.5 micron.

24. A process as in claim 20 wherein said illumination steps are repeated until substantially all of the small particles have been exploded and fragments of the small particles have been exploded to produce smaller fragments until substantially all of the fragments remaining in the hair ducts are smaller than 0.1 micron.

25. A process as in claim 20 wherein said contaminant is applied in such a manner as to leave a thin film of contaminant on the surface of the skin section prior to said illumination step (b), said illumination step (b) having sufficient energy to explode a substantial number of the particles in said thin film so as to define a footprint of the initial illumination.

26. A process as in claim 20 wherein said short pulse of light defines a pulse duration, and the pulse duration measured at one half maximum power of the pulse is no longer than 30 nanoseconds.

27. A process as in claim 20 and further comprising an additional step between steps (b) and (c) of applying to said skin section a fluid transparent to light at said frequency band of high absorption, said application being performed in a manner so as to assure that at least a portion of said fluid infiltrates said hair ducts.

28. A process as in claim 27 wherein said fluid has an index of refraction which is greater than the index of refraction of said skin.

* * * * *